United States Patent
Shaw

(10) Patent No.: US 6,441,229 B1
(45) Date of Patent: Aug. 27, 2002

(54) PROCESS FOR THE PREPARATION OF HIGHER-ALKANE SULFONYL HALIDES

(75) Inventor: James E. Shaw, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/602,231

(22) Filed: Jun. 23, 2000

(51) Int. Cl.[7] ............................................. C07C 309/00
(52) U.S. Cl. ...................................... 562/829; 562/828
(58) Field of Search ................................ 562/828, 829

(56) References Cited

U.S. PATENT DOCUMENTS

| | | | |
|---|---|---|---|
| 4,699,736 A | * | 10/1987 | Gongora et al. |
| 4,705,799 A | | 11/1987 | Gregory ..................... 514/376 |
| 4,956,494 A | * | 9/1990 | Husain et al. |
| 5,500,405 A | | 3/1996 | Rosen et al. ................. 504/195 |

OTHER PUBLICATIONS

CA:130:95292 abs of Youji Huaxue by Kang 18(6) pp 559–561 1998.*
CA:127:333071 abs of Jingxi Huagong by Pan et al 14(5) pp 53–55 1997.*
CA:100:191690 abs of J Org Chem by Van der Broek et al 49(10) p1691–5 1984*
CA:122:290344 abs of JP0636043 Nov. 1994.*

* cited by examiner

Primary Examiner—Jean F. Vollano
(74) Attorney, Agent, or Firm—Charles W. Stewart

(57) ABSTRACT

Higher-alkane sulfonyl halides are prepared by contacting a sulfur-containing compound, a halogen-containing compound, and a phase transfer agent within a reaction zone under reaction conditions.

7 Claims, No Drawings

PROCESS FOR THE PREPARATION OF HIGHER-ALKANE SULFONYL HALIDES

The present invention relates to a method for preparing alkane sulfonyl halides. More particularly, this invention concerns a method for producing higher-alkane sulfonyl chlorides through the oxidation of alkyl mercaptans or dialkyl disulfides while inhibiting the formation of undesirable byproducts.

BACKGROUND OF THE INVENTION

Alkane sulfonyl halides, particularly alkane sulfonyl chlorides, are know for their utility in imparting functionality into various compounds or as intermediates to modify various compounds, including pharmaceuticals, agriculture chemicals, photographic chemicals and the like, in order to increase their efficacy, to protect sensitive functional groups during certain processing steps, or to improve the recovery and purity during isolation procedures.

A number of prior-art methods are known for preparing alkane sulfonyl halides, particularly methane sulfonyl chloride. A known preparation process for methane sulfonyl chloride involves the reaction of chlorine with methyl mercaptan or dimethyl disulfide in an aqueous solution of hydrogen chloride. The products of such reaction generally include methane sulfonyl chloride, hydrogen chloride, and at least one undesirable byproduct.

When methyl mercaptan or dimethyl disulfide is employed as a reactant to produce a methane sulfonyl halide, the amount of undesirable byproducts is minimal. However, when higher-alkyl mercaptans or higher-alkyl disulfides are employed as reactants to produce higher-alkane sulfonyl halides, the quantity of undesirable byproducts, such as alpha-chlorinated byproducts, is greatly increased. The presence of such undesirable byproducts causes the process to be less efficient and can necessitate the implementation of expensive separation processes and equipment.

SUMMARY OF THE INVENTION

An object of the present invention is to provide a more efficient process for preparing higher-alkane sulfonyl halides.

A further object of the present invention is to provide a process for preparing higher-alkane sulfonyl halides which inhibits the formation of at least one undesirable byproduct.

Other objects and advantages of the present invention will become more apparent as the invention is more fully disclosed hereinbelow.

In accordance with the present invention, there is provided a process for preparing higher-alkane sulfonyl halides comprising contacting a sulfur-containing compound, a halogen-containing compound, and a phase transfer agent within a reaction zone under conditions sufficient to produce a higher-alkane sulfonyl halide.

DETAILED DESCRIPTION OF THE INVENTION

As used herein, the term "higher-alkane" means an alkane having 2 or more carbon atoms, preferably 2 to 20 carbon atoms.

It has been discovered that, in a process for producing higher-alkane sulfonyl halides by reacting a sulfur-containing compound and a halogen-containing compound, the presence of a phase transfer agent during such reaction inhibits the production of certain undesirable byproducts.

Thus, in accordance with an embodiment of the present invention, a sulfur-containing compound, a halogen-containing compound, and phase transfer agent are contacted within a reaction zone under reaction conditions sufficient to produce a higher-alkane sulfonyl halide.

The sulfur-containing compound employed in the process of the present invention can generally be represented by the formula RSX, wherein X is hydrogen or a radical of the formula $SR^1$ and where R is an alkyl group having 2 to 20 carbon atoms, preferably 3 to 12 carbon atoms, and $R^1$ is an alkyl group having 1 to 20 carbon atoms, preferably 1 to 12 carbon atoms. R and $R^1$ can be the same or different alkyl groups, but are preferably the same. The alkyl groups may be branched or straight-chained and may also be substituted alkyl radicals having such substituent atoms and groups as hydroxyl, chlorine, bromine, fluorine, amine ($NH_2$), sulfonic acid ($SO_3H$), sulfonyl chloride ($SO_2Cl$), and $SO_3R$. However, the alkyl groups are preferably not substituted directly with halogens. More preferably, both alkyl groups, R and R', are unsubstituted.

Preferred sulfur-containing compounds include ethyl mercaptan, n-propyl mercaptan, isopropyl mercaptan, n-butyl mercaptan, n-hexyl mercaptan, cyclohexyl mercaptan, n-octyl mercaptan, n-nonyl mercaptan, n-decyl mecaptan, n-dodecyl mercaptan, diethyl disulfide, di-n-propyl disulfide, di-iso-propyl disulfide, di-n-butyl disulfide, di-iso-butyl disulfide, di-n-hexyl disulfide, di-iso-hexyl disulfide, di-n-octyl disulfide, di-iso-octyl disulfide, and combinations of any two or more thereof. More preferably, the sulfur-containing compound is n-propyl mercaptan, n-octyl mercaptan, di-n-propyl disulfide, di-n-octyl disulfide or a combination of two or more thereof. Most preferably, the sulfur-containing compound is n-octyl mercaptan.

The halogen-containing compound employed in the process of the present invention can be any halogen-containing compound suitable for reacting with the sulfur-containing compound to produce the desired alkane sulfonyl halide product of this invention. Preferably, the halogen of the halogen-containing compound is chlorine or bromine, but more preferably it is chlorine. Most preferably, the halogen-containing compound is chlorine ($Cl_2$).

The amount of halogen-containing compound employed in the process of the present invention can be the stoichiometric amount suitable for reacting with the sulfur-containing compound to yield the desired alkane sulfonyl halide. Generally, the weight ratio of halogen-containing compound to sulfur-containing compound employed in the present inventive process is from about 1:10 to about 100:1, but can be from about 1:2 to about 20:1, or from about 1:1 to about 8:1, or from 2:1 to 4:1.

The sulfur-containing compound and halogen-containing compound are preferably contacted within a reaction zone in the presence of an aqueous hydrogen halide. Preferably, the aqueous hydrogen halide comprises hydrochloric acid, hydrobromic acid, or a mixture thereof. Most preferably, the aqueous hydrogen halide comprises hydrochloric acid. The weight of the hydrogen halide as a percentage of the total weight of the aqueous hydrogen halide is preferably from about 5 weight percent to about 80 percent, more preferably from about 10 to about 50 percent, more preferably from about 20 to about 40 percent, most preferably from 25 to 35 percent.

The amount of aqueous hydrogen halide employed in the process present invention can be any amount which is effective to produce the desired alkane sulfonyl halide product. Preferably, the amount of aqueous hydrogen halide is such that the weight ratio of the hydrogen halide in the aqueous hydrogen halide to the sulfur-containing compound is from about 1:25 to about 50:1, more preferably from about 1:5 to about 10:1, and most preferably from 1:3 to 6:1.

Generally, the phase transfer agent employed in the process of the present invention comprises one or more compounds capable of inhibiting the formation of undesirable byproducts and promoting the yield of desired sulfonyl halide.

A preferred phase transfer agent for use in the reaction system of the instant invention is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of two or more thereof.

The presently preferred phase transfer agent is an alkoxylated compound. Examples of suitable alkoxylated compounds include, but are not limited to, alkoxylated alcohols, alkoxylated mercaptans, sulfates of alkoxylated alcohols, alkoxylated phenols, sulfates of alkoxylated phenols, and combinations of two or more thereof.

An alkoxylated alcohol useful in the present invention has a general formula of $R^2O[CH_2CH(R^3)O]_qH$ where $R^2$ is a $C_1$–$C_{20}$ hydrocarbyl radical selected from the group consisting of alkyl radical, alkylaryl radical, aryl radical, cycloalkyl radical, alkenyl radical, and combinations of two or more thereof, preferably $R^2$ is a $C_6$–$C_{18}$ alkyl radical, most preferably $R^2$ is a $C_{10}$–$C_{16}$ alkyl radical; $R^3$ is selected from the group consisting of hydrogen, $C_1$–$C_{16}$ alkyl radicals, $C_2$–$C_{16}$ alkenyl radicals, and combinations of two or more thereof, preferably $R^3$ is a hydrogen or a $C_1$–$C_3$ alkyl radical, most preferably $R^3$ is hydrogen; and q is an integer of from 1 to about 20, preferably from about 2 to about 12, most preferably from 5 to 10. An example of suitable alkoxylated alcohol is TERGITOL® 15-S-7. TERGITOL® 15-S-7 is an ethoxylated alcohol, manufactured and marketed by Union Carbide Corporation, having the formula of $R^2O(CH_2CH_2O)_7H$ where $R^2$ is a secondary alkyl radical having 11–15 carbon atoms and 7 is the averaged number of the ethylene oxide units. Other suitable alkoxylated alcohols are also available from Union Carbide Corporation.

A sulfate of alkoxylated alcohol useful in the present invention has a general formula of $R^2O[CH_2CH(R^3)O]_qSO_3M$ where $R^2$, $R^3$, and q are the same as those described above and M is an alkali metal or an alkaline earth metal or combinations of two or more thereof. An example of suitable sulfate of alkoxylated alcohol is sodium sulfate of an ethoxylated alcohol having the formula of $R^2O(CH_2CH_2O)_qSO_3Na$ in which $R^2$ and q are the same as those disclosed above.

Useful alkoxylated phenols and sulfates of alkoxylated phenols can have general formulas of $(R^3)_pArO[CH_2CH(R^3)O]_qH$ and $(R^2)_pArO[CH_2CH(R^3)O]_qSO_3M$, respectively where $R^2$, $R^3$, q and M are the same as those disclosed above, Ar is an aryl group, preferably a phenyl group, and p is an integer ranging from 0 to 5. Examples of these alkoxylated phenols are ethoxylated phenol $ArO(CH_2CH_2O)_qH$ and sodium sulfate of ethoxylated phenol $ArO(CH_2CH_2O)_qSO_3$ Na where Ar and q are the same as disclosed above.

An alkoxylated mercaptan useful in the present invention has a general formula of $R^2S[CH_2CH(R^3)O]_qH$ where $R^2$, $R^3$, and q are the same as those described above. An example of an alkoxylated mercaptan is an ethoxylated mercaptan having the formula of $R^2S(CH_2CH_2O)_7H$ where $R^2$ is primarily a tertiary dodecyl group and 7 is the averaged number of ethylene oxide units. This ethoxylated mercaptan is a surfactant, available under the trade name AQUA-CLEEN®II (Phillips Petroleum Company, Bartlesville, Okla.). Another example is an ethoxylated thiophenol having the same number of ethylene oxide units. Other suitable alkoxylated mercaptans are also available from Phillips Petroleum Company.

Quaternary ammonium salts useful in the present invention have the general formula $(R^4)_4N^+X^-$ where $R^4$ is an alkyl radical of from 1 to 20 carbon atoms; and X is selected from the group consisting of $Br^-$, $Cl^-$, $I^-$, $F^-$, $R^4CO_2^-$, $QSO_3^-$, $BF_4^-$, and $HSO_4^-$, where Q is an aryl, alkaryl or arylalkyl radical of 6 to 10 carbon atoms. It will be noted that a variety of anions are suitable as the component of the quaternary ammonium salts.

Useful quaternary ammonium salts according to the general formula given above include, but are not limited to, methyltrialkyl($C_8$–$C_{10}$) ammonium chloride (also known as ADOGEN 464 ®, Aldrich Chemical Company), cetyltrimethylammonium bromide, hexadecyltrimethylammonium bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutylammonium fluoride, tetrabutylammonium tetrafluoroborate, and combinations of two or more thereof.

An alkali metal alkyl sulfate of the general formula of $R^4OSO_3M$ can be used in the present invention, wherein $R^4$ and M are the same as those disclosed above. Examples of suitable compounds according to the general formula for the alkali metal alkyl sulfates include, but are not limited to, lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate, and combinations of two or more thereof.

Useful alkali metal salts of alkanoic acids have the general formula of $R^4CO_2M$, where $R^4$ and M have the same meaning as given above. Examples of suitable alkali metal salts of alkanoic acids include, but are not limited to, lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and combinations of two or more thereof.

Useful alkali metal salts of alkaryl sulfonic acids have the general formula of $(R^4)_p ArSO_3M$ where $R^4$ and M are the same as those disclosed above, Ar is an aryl group or a phenyl group, and p is an integer ranging from 0 to 5. Typical compounds within such group include, but are not limited to, sodium dodecylbenzenesulfoante, potassium dodecylbenzenesulfonate, lithium dodecylbenzenesulfonate, sodium tetradecylbenzenesulfonate, potassium hexadecylbenzenesulfoante, rubidium dodecylbenzenesulfoante, cesium dodecylbenzenesulfonate, sodium octadecylbenzenesulfoante, potassium octadecylbenzenesulfonate, soidum eicosylbenzenesulfonate, and combinations of two or more thereof.

Examples of suitable 1-alkyl pyridinium salts include, but are not limited to, 1-dodecylpyridinium paratoluenesulfonate, 1-dodecylpyridinium chloride, 1-hexadecylpyridinium chloride, 1-hexadecylpyridinium paratoluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and combinations of two or more thereof.

The amount of the phase transfer agent employed in the present inventive process can be any amount which inhibits the formation of undesirable byproducts and/or promotes the formation of the desired sulfonyl halide. Preferably, the amount of phase transfer agent employed gives a weight ratio of phase transfer agent to sulfur-containing compound of from about 1:1,000 to about 1:1, preferably from about 1:500 to about 1:3, and most preferably from 1:300 to 1:5.

The sulfur-containing compound, halogen-containing compound, and phase transfer agent can be contacted in any suitable reaction vessel. The contacting conditions can be any conditions sufficient to produce the desired alkane sulfonyl halide. Usually, the reaction is carried out at substantially atmospheric pressure, while either atmospheric pressure or reduced pressure may be used in the purification steps. The reaction temperature is generally from about $-10°$ C. to about 50° C., preferably from about 25° C. to about 35° C. The process can be carried out either batchwise or continuously.

The product produced by the process of the present invention comprises a higher-alkane sulfonyl halide. Preferably, the higher-alkane sulfonyl has the formula $RSO_2Y$, wherein Y is chlorine or bromine, preferably chlorine; and R is an alkane having 2 to 20 carbon atoms, more preferably 3–12 carbon atoms, and most preferably 8 carbon atoms. Preferred higher-alkane sulfonyl halides include propane sulfonyl chloride, butane sulfonyl chloride, hexane sulfonyl chloride, octane sulfonyl chloride, nonane sulfonyl chloride, decane sulfonyl chloride, dodecane sulfonyl chloride, and combinations of two or more thereof. Most preferably, the higher-alkane sulfonyl halide is octane sulfonyl chloride.

The product produced by the present invention may further comprise at least one undesirable by product; however, the amount of such byproduct in the product produced by the present inventive process is less than the amount of such byproduct in a product produced when a phase transfer agent, such as those used in the inventive process, is not used. The undesirable byproduct whose formation is inhibited by the process of the present invention can be, for example, an alpha-chlorinated compound, generally an alpha-chloroalkane sulfonyl halide corresponding to the desired higher-alkane sulfonyl halide product.

The product of the present inventive process may be subjected to further recovery, separation, and purification processes known in the art in order to recover a substantially pure higher-alkane sulfonyl halide product.

The following example is provided to further illustrate the practice of the present invention and is not intended to limit the scope of the invention of the claims.

EXAMPLE

This example demonstrates that the present inventive method of producing higher-alkane sulfonyl halides, which employs a phase transfer agent, results in a product having less undesirable byproducts and/or more desired higher-alkane sulfonyl halide than methods which do not employ a phase transfer agent.

To a 250 ml, three-necked flask equipped with thermowell, magnetic stirring bar, gas dispersion tube, and dry ice (isopropanol) condenser with $N_2$ inlet/outlet on top, was added the appropriate amounts of mercaptan, TERGITOL 15-S-7® (Union Carbide) phase transfer agent and aqueous hydrogen chloride. The amounts of the reagents and catalyst added to the flask are provided in Table 1.

Aluminum foil covered the flask and condenser and lights were dimmed to avoid exposure to light during the reactions since light promotes alpha-chlorination. The flask was placed in an ice water bath, and chlorine was bubbled into the rapidly stirred reaction mixture through the gas dispersion tube over 25 to 30 minutes. The temperature of the reaction was maintained at approximately 20° C. to 30° C. In all runs, excess chlorine (3 grams or more) was used to obtain the best conversion to alkane sulfonyl chloride. The total chlorine used for each run is given in Table 1.

After all the chlorine was added, the ice water bath was removed from around the flask, and the reaction mixture was stirred an additional 3 minutes. The dry ice was removed from the condenser and replaced with room temperature water and stirring continued about 2 minutes. $N_2$ was slowly bubbled through the reaction mixture using the gas dispersion tube for 5 minutes with slow stirring. $N_2$ exiting the flask was scrubbed free of HCl and $Cl_2$ using a water trap or scrubber. The stirring was stopped and the phases allowed to separate.

The octane sulfonyl chloride phase was on top of the aqueous HCl phase, but for propane sulfonyl chloride and ethane sulfonyl chloride, the sulfonyl chloride phases were below the aqueous HCl phase. In the case of propane sulfonyl chloride and ethane sulfonyl chloride, not all the sulfonyl chloride separated out.

Material balance calculations revealed that about 8 percent of the sulfonyl chloride was dissolved in the aqueous HCl phase. To recover this part of the sulfonyl chloride, the aqueous HCl phase was extracted with chloroform (10 ml to 20 ml). The alkane sulfonyl chloride phases were analyzed neat or as chloroform solutions by gas chromatograph. Gas chromatograph analyses were carried out on a Hewlett Packard 6890 instrument using a 10 m×0.53 mm ID HP-1 (methyl siloxane or methyl silicone) capillary column (injection port 250° C., column temperature initially 50° C. for 1 minute, then 20° C./minute to 200° C., and then maintained at 200° C., flame ionization detector). Compositions for the crude products from each run are reported in Table 1.

TABLE 1

Higher-Alkane Sulfonyl Chloride Preparation

| | | Amounts of Reagents and Catalyst | | | Crude Product | |
|---|---|---|---|---|---|---|
| | | Wt. | Wt. | Wt. | Composition (Wt. %) | |
| Run | Mercaptan | Wt. (g) | Tergitol (g) | 30% HCl (g) | Chlorine (g) | % RSO$_2$Cl | % R'CHClSO$_2$Cl |
| 1 | ethyl | 6.6 | 0 | 40 | 25.7 | 98.0 | 0.44 |
| 2 | ethyl | 6.6 | 0 | 40 | 25.7 | 97.7 | 0.87 |
| 3 | ethyl | 6.6 | 0.04 | 40 | 26.6 | 98.2 | 0.34 |
| 4 | ethyl | 6.6 | 0.30 | 40 | 25.5 | 97.5 | 0.40 |
| 5 | ethyl | 6.6 | 0.37 | 40 | 26.2 | 97.1 | 0.29 |
| 6 | n-propyl | 5.4 | 0 | 100[a] | 17.3 | 91.0 | 8.5 |
| 7 | n-propyl | 8.1 | 0 | 40 | 25.9 | 89.8 | 6.4 |
| 8 | n-propyl | 8.1 | 0.04 | 40 | 26.1 | 97.2 | 0.98 |
| 9 | n-propyl | 8.1 | 0.22 | 40 | 26.2 | 97.2 | 0.18 |
| 10 | n-propyl | 8.1 | 0.80 | 40 | 25.7 | 98.1 | 0.34 |
| 11 | n-octyl | 15.0 | 0 | 90[b] | 33.2 | 43.9[c] | 24.7 |
| 12 | n-octyl | 20.0 | 0.4 | 30 | 34.8 | 94.1 | 0.95 |
| 13 | n-octyl | 20.0 | 0.8 | 30 | 36.6 | 93.4 | 1.17 |
| 14 | n-octyl | 10.0 | 1.4 | 60[b] | 17.6 | 97.1 | 0.07 |

[a]Concentration of hydrochloric acid solution was 33.7%.
[b]Concentration of hydrochloric acid solution was 37.5%.
[c]In addition to 43.9% RSO$_2$Cl, there was 14.8% of sulfinyl chloride, RSOCl. Runs 12 to 14 had only 0.15–0.33% RSOCl.

Runs 1, 2, 6, 7, and 11 illustrate a method of making alkane sulfonyl chlorides without employing a phase transfer agent. Runs 3–5, 8–10, and 12–14 illustrate a method of making alkane sulfonyl chlorides using a phase transfer agent, in accordance with the present invention.

This example illustrates that the inventive process significantly inhibits the formation of alpha-chlorinated byproducts (R'CHClSO$_2$Cl) versus a process not using a phase transfer agent. In addition, the inventive process can increase production of the desired higher-alkane sulfonyl chloride product versus the conventional process.

While this invention has been described in detail for the purpose of illustration, it should not be construed as limited thereby but intended to cover all changes and modifications within the spirit and scope thereof.

What is claimed is:

1. A process for making an alkane sulfonyl halide, said process comprises:

contacting within a reaction zone and under suitable reaction conditions a halogen-containing compound selected from the group consisting of chlorine and bromine with a sulfur-containing compound of the formula RSH, wherein R is an alkyl group having from three to twelve carbon atoms, in the presence of both an aqueous hydrogen halide selected from the group consisting of aqueous hydrochloric acid and aqueous hydrobromic acid and an alkoxylated compound phase transfer agent selected from the group consisting of alkoxylated alcohols, alkoxylated mercaptans, sulfates of alkoxylated alcohols, alkoxylated phenols, sulfates of alkoxylated phenols and combinations of two or more thereof, whereby said alkane sulfonyl halide is formed.

2. A process according to claim 1 wherein the weight ratio of said alkoxylated compound phase transfer agent to said sulfur-containing compound is from about 1:1000 to about 1:1.

3. A process according to claim 2 wherein the weight ratio of said halogen-containing compound to said sulfur-containing compound is from about 1:25 to about 50:1.

4. A process according to claim 3 wherein said alkoxylated compound phase transfer agent is an alkoxylated alcohol.

5. A process according to claim 4 wherein the contacting of said halogen-containing compound with said sulfur-containing compound is conducted at a temperature from about −10° C. to about 50° C.

6. A process according to claim 1 wherein the weight ratio of said alkoxylated compound phase transfer agent to said sulfur-containing compound is from about 1:500 to about 1:3.

7. A process according to claim 6 wherein the weight ratio of said halogen-containing compound to said sulfur-containing compound is from about 1:5 to about 10:1.

* * * * *